(12) United States Patent
Nitta (10) Patent No.: US 6,201,223 B1
(45) Date of Patent: Mar. 13, 2001

(54) HUMIDIFICATION CONTROL UNIT AND METHOD OF MANUFACTURING SAME

(75) Inventor: Kazufuku Nitta, Saitama-Ken (JP)

(73) Assignee: Respironics, Inc., Pittsburgh, PA (US)

( * ) Notice: Subject to any disclaimer, the term of this patent is extended or adjusted under 35 U.S.C. 154(b) by 0 days.

(21) Appl. No.: 09/242,584

(22) PCT Filed: Aug. 20, 1998

(86) PCT No.: PCT/JP97/02892

§ 371 Date: Aug. 23, 1999

§ 102(e) Date: Aug. 23, 1999

(87) PCT Pub. No.: WO98/08032

PCT Pub. Date: Feb. 26, 1998

(30) Foreign Application Priority Data

Aug. 23, 1996 (JP) .................................................. 8-222724

(51) Int. Cl.[7] ........................................................ H05B 3/44
(52) U.S. Cl. ............................ 219/544; 392/397; 392/482
(58) Field of Search ..................................... 219/534, 535, 219/544; 392/479, 482, 396, 397; 128/203.17, 203.27, 204.17

(56) References Cited

U.S. PATENT DOCUMENTS

| 1,446,807 | * | 2/1923 | Mercer ................................. 392/482 |
| 3,414,863 | * | 12/1968 | Lemelson ............................. 392/479 |
| 3,501,619 | | 3/1970 | Buiting et al. . |
| 3,507,627 | * | 4/1970 | Frant et al. .......................... 392/482 |
| 3,582,968 | * | 6/1971 | Buiting ................................ 392/482 |
| 3,607,131 | | 9/1971 | Williams et al. . |
| 3,616,796 | | 11/1971 | Jackson . |
| 3,659,604 | | 5/1972 | Melville et al. . |
| 3,688,083 | | 8/1972 | Rice et al. . |
| 3,695,267 | | 10/1972 | Hirtz et al. . |
| 3,707,966 | | 1/1973 | Nebel . |
| 3,747,598 | | 7/1973 | Cowans . |
| 3,834,682 | | 9/1974 | McPhee . |
| 3,871,373 | | 3/1975 | Jackson . |
| 3,916,891 | | 11/1975 | Freytag et al. . |
| 3,934,117 | | 1/1976 | Schladitz . |
| 3,948,316 | * | 4/1976 | Souriau ................................ 392/396 |
| 3,954,920 | | 5/1976 | Heath . |

(List continued on next page.)

FOREIGN PATENT DOCUMENTS

| 0009543 | 4/1980 | (EP) . |
| 0299381 | 1/1989 | (EP) . |
| 0413127 | 2/1991 | (EP) . |
| 2250542 | 6/1975 | (FR) . |
| 2636845 | 3/1990 | (FR) . |
| 2176405 | 12/1986 | (GB) . |
| 3-125832 | 5/1991 | (JP) . |
| 4-86437 | 3/1992 | (JP) . |
| 7-301440 | 11/1995 | (JP) . |
| WO 92/07601 | 5/1992 | (WO) . |

*Primary Examiner*—Teresa Walberg
*Assistant Examiner*—Fadi M. Dahbour
(74) *Attorney, Agent, or Firm*—Reed Smith LLP (57) ABSTRACT

A humidity regulating unit including a heating element housed inside a covering that has a porous retaining wall through which water does not pass but steam or gas passes. In one embodiment, the covering has several bulges along the circumference of the heating element that protrudes outward from the outer surface of heating element to form several water routes along the outer surface of heating element. The covering and the outer surface of heating element are bonded between adjacent water routes so that the outer surface of heating element is used as part of the wall of the water routes. As a result, the size of heating element does not restrict making the cross section of each water route as small as possible, and even if the covering breaks, the amount of water leaking from the humidity regulating unit is minimized.

21 Claims, 6 Drawing Sheets

U.S. PATENT DOCUMENTS

| | | |
|---|---|---|
| 3,990,441 | 11/1976 | Hoyt et al. . |
| 4,010,748 | 3/1977 | Dobritz . |
| 4,014,382 | 3/1977 | Heath . |
| 4,028,445 | 6/1977 | Hickmann et al. . |
| 4,048,993 | 9/1977 | Dobritz . |
| 4,062,359 | 12/1977 | Geaghan . |
| 4,068,625 | 1/1978 | Brown . |
| 4,086,305 | 4/1978 | Dobritz . |
| 4,098,852 | 7/1978 | Christen et al. . |
| 4,110,419 | 8/1978 | Miller . |
| 4,146,597 | 3/1979 | Eckstein et al. . |
| 4,155,961 | 5/1979 | Benthin . |
| 4,187,390 | 2/1980 | Gore . |
| 4,190,046 * | 2/1980 | Virag ..................................... 392/397 |
| 4,195,044 | 3/1980 | Miller . |
| 4,201,204 | 5/1980 | Rinne et al. . |
| 4,225,542 | 9/1980 | Wall et al. . |
| 4,248,217 | 2/1981 | Brisson . |
| 4,300,925 | 11/1981 | Nikandrov et al. . |
| 4,303,601 | 12/1981 | Grimm et al. . |
| 4,305,388 | 12/1981 | Brisson . |
| 4,318,398 | 3/1982 | Oetjen et al. . |
| 4,327,717 | 5/1982 | Oetjen et al. . |
| 4,355,636 | 10/1982 | Oetjen et al. . |
| 4,367,734 | 1/1983 | Benthin . |
| 4,369,777 | 1/1983 | Lwoff et al. . |
| 4,381,267 | 4/1983 | Jackson . |
| 4,427,004 * | 1/1984 | Miller ..................................... 392/397 |
| 4,430,994 | 2/1984 | Clawson et al. . |
| 4,436,674 | 3/1984 | McMenamin . |
| 4,461,735 | 7/1984 | Wirt . |
| 4,477,395 | 10/1984 | Albarda . |
| 4,480,172 | 10/1984 | Ciciliot et al. . |
| 4,532,088 | 7/1985 | Miller . |
| 4,564,748 | 1/1986 | Gupton . |
| 4,621,632 | 11/1986 | Bartels et al. . |
| 4,621,633 | 11/1986 | Bowles et al. . |
| 4,629,590 * | 12/1986 | Bagwell .............................. 392/397 |
| 4,652,408 | 3/1987 | Montgomery . |
| 4,657,713 | 4/1987 | Miller . |
| 4,674,494 | 6/1987 | Wiencek . |
| 4,676,237 | 6/1987 | Wood et al. . |
| 4,682,010 | 7/1987 | Drapeau et al. . |
| 4,704,988 | 11/1987 | Mellet . |
| 4,708,831 | 11/1987 | Elsworth . |
| 4,753,758 | 6/1988 | Miller . |
| 4,770,168 | 9/1988 | Rusz et al. . |
| 4,771,770 | 9/1988 | Artemenko et al. . |
| 4,774,032 | 9/1988 | Coates et al. . |
| 4,822,533 | 4/1989 | Steiner et al. . |
| 4,829,997 | 5/1989 | Douwens et al. . |
| 4,829,998 | 5/1989 | Jackson . |
| 4,861,523 | 8/1989 | Beran . |
| 4,910,384 | 3/1990 | Silver . |
| 4,921,642 | 5/1990 | La Torraca . |
| 4,943,704 | 7/1990 | Rabenau et al. . |
| 5,062,145 | 10/1991 | Zwaan et al. . |
| 5,109,471 | 4/1992 | Lang . |
| 5,148,801 | 9/1992 | Douwens et al. . |
| 5,163,423 | 11/1992 | Suzuki . |
| 5,172,686 | 12/1992 | Anthony . |
| 5,195,515 | 3/1993 | Levine . |
| 5,218,833 | 6/1993 | Newbold . |
| 5,226,411 | 7/1993 | Levine . |
| 5,255,674 | 10/1993 | Oftedal et al. . |
| 5,257,341 | 10/1993 | Austin, Jr. et al. . |
| 5,271,086 * | 12/1993 | Kamiyama et al. ................. 392/482 |
| 5,273,689 | 12/1993 | Hamasaki . |
| 5,318,731 | 6/1994 | Yokoya et al. . |
| 5,336,156 | 8/1994 | Miller et al. . |
| 5,348,691 | 9/1994 | McElroy et al. . |
| 5,349,946 | 9/1994 | McComb . |
| 5,357,948 | 10/1994 | Eilentropp . |
| 5,367,604 | 11/1994 | Murray . |
| 5,383,447 | 1/1995 | Lang . |
| 5,389,311 | 2/1995 | Hetzel . |
| 5,392,770 | 2/1995 | Clawson et al. . |
| 5,399,299 | 3/1995 | Stengel et al. . |
| 5,435,298 | 7/1995 | Anthony . |
| 5,462,048 | 10/1995 | Lambert et al. . |
| 5,537,996 | 7/1996 | McPhee . |
| 5,592,933 | 1/1997 | Zucchi . |
| 5,624,610 | 4/1997 | Yokoya et al. . |
| 5,640,951 | 6/1997 | Huddart et al. . |
| 5,647,344 | 7/1997 | Turnbull . |
| 5,653,920 | 8/1997 | DiDomenico . |

* cited by examiner

HUMIDIFICATION CONTROL UNIT AND METHOD OF MANUFACTURING SAME

BACKGROUND OF THE INVENTION

1. Field of the Invention

This invention pertains to a humidity regulating unit and to a method of manufacturing a humidity regulating unit.

2. Description of the Related Art

Japanese Unexamined Patent Appl. No. 62-26076 discloses a humidity regulating unit in which a tube is used to carry water over a heating element. The tube has a porous retaining wall as the main wall through which water does not pass but steam passes. This humidity regulating unit is designed such that an electric heating element (with a diameter of at least 3 mm) is arranged inside the tube by preparing one tube with a somewhat large diameter. During use, this water carrying tube is connected to a water supply source such that the tube is always filled with water. Steam is expelled through the porous retaining wall of the water carrying tube by the heat of the electric heating element.

When this type of humidity regulating unit is used inside the inhalation route (inhalation circuit) of an artificial respirator, for example, not only can it assure humidifying performance, but using the fact that the outer shape of the humidity regulating unit is a tube, the humidity regulating unit can be arranged in the inhalation route and does not require a large-volume chamber for a humidifier.

However, in the humidity regulating unit described above, from considerations such as assuring adequate steam generation and the size of the heating element, a water carrying tube that has a somewhat large diameter must be used. If the water carrying tube is broken, an impermissible amount of water inevitably leaks which can cause various problems. When the humidity regulating unit is used in the inhalation route of an artificial respirator, for example, water leakage has the undesirable effect of reducing humidifying performance and the leaking water itself can flow to the inhalation side of the inhalation circuit, which is the side where the user of the artificial respirator is located.

SUMMARY OF THE INVENTION

This invention was developed upon reflecting on the situation described above. Its first object is to offer a humidity regulating unit that even if it breaks, can markedly reduce problems caused by leakage while maintaining previous humidifying performance.

A second object of this invention is to offer a method for manufacturing such a humidity regulating unit.

These objects are achieved by providing a humidity regulating unit that includes a heating element housed in a covering that has a porous retaining wall through which water does not pass but steam passes. Several independent water routes are formed in succession between the outer wall of the above-mentioned heating element and the above-mentioned covering by cooperative action between the outer wall of the heating element and the covering where open spaces between the covering and the heating element are provided along the circumference of the heating element.

The latter object is achieved by providing a method of manufacturing a humidity regulating unit that includes preparing two halves of a covering defined by a porous retaining wall through which water cannot pass but steam passes. The two halves are laminated onto opposing sides of a heating element such that at least one independent water route is formed between each half and the outer wall of the heating element by cooperative action between each half and the outer wall of the heating element, where open spaces between the covering and the heating element are provided along the circumference of the heating element. Then each of the above-mentioned halves of the covering and the outer wall of the above-mentioned heating element are bonded to define the water routes along the heating element.

The latter object is also achieved by providing a method of manufacturing a humidity regulating unit that includes providing a tubular covering defined by a porous retaining wall through which water cannot pass but steam passes and a cap that can cover an open side of the covering.

A heating element is placed within the above-mentioned covering and several independent water routes are formed in succession between the covering and the outer wall of the heating element by cooperative action between the covering and the outer wall of the heating element, such that open spaces are provided between the covering and the heating element along the circumference of the heating element.

The above-mentioned covering and the outer wall of the above-mentioned heating element are bonded to define water routes between the bulges in the heating element. The open side of the above-mentioned covering is then covered by the abovementioned cap. Because a heating element is housed in a covering that has a porous retaining wall through which water does not pass but steam passes and independent water routes are formed between the outer wall of the heating element and the covering by cooperative action between the outer wall of the heating element and the covering by providing spaces along the circumference of the heating element, when water is supplied into each water route and heated by the heating element, steam is expelled from each water route through the porous retaining wall, and the desired humidifying performance can be achieved under optimum conditions.

In addition, because the outer surface of the heating element is used as part of the wall of the water routes and the heating element does not have to be housed inside the water routes, the size of the heating element does not restrict making the cross section of each water route as small as possible. As a result, even if the covering breaks or is damaged, the amount of water leaking from the water routes that this covering covers is minimized, and water leakage can be reduced to the extent that there is no substantial decrease in humidifying performance or problems associated with excessive water leakage.

Because the humidifying unit in one embodiment of this invention has several bulges in the covering along the circumference of the heating element that protrudes outward from the outer surface of the heating element, each water route is comprised of a bulge and the outer surface of the heating element that covers the open base end of the bulge. In addition to having the desirable leak minimization effects described above, the surface area of the steam emitting surface is increased by each bulge, and humidifying performance is improved.

In another embodiment of the present invention, channels are formed in the outer surface of the heating element by providing spaces along the circumference of the heating element. In this embodiment, each water route is defined by the channel and the covering that covers the opening of the channel. In addition to having the desirable leak minimizing effects described above, the proportion of the outer wall of the heating element that comprises the side walls of each water route is increased, and by making the shape of the water routes more stable, the stability of humidifying performance can be increased. As a result, this humidity regulating unit can be used in regions that have higher speed flow.

In yet another embodiment of the present invention, the covering and the outer surface of the heating element are bonded between adjacent water routes, the independence of each water route can be assured and the leak minimizing effects described above can be achieved more securely.

The present invention also contemplates that the outer surface of the heating element is formed by a coating resin and the covering is welded to the coating resin of the heating element. By taking advantage of the easy bonding between these two (the covering generally is formed by a resin such as polytetrafluoroethylene), the covering and the outer surface of the heating element can be bonded easily.

In a further embodiment, the heating element is an electric heating element and the coating resin is an insulator for this electric heating element. The covering is welded to the outer surface of the heating element using the insulator of the electric heating element.

The present invention also contemplates that the humidity regulating unit can include several independent water routes in succession between the outer surface of the heating element and the covering by providing spaces along the circumference of the heating element, for example by bonding two halves or the like.

The present invention further contemplates that the humidity regulating unit can include several independent water routes are formed in succession between the outer surface of the heating element and the covering by providing spaces along the circumference of the heating element that are formed by placing the heating element inside the covering.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

FIGS. 1 to 5 show a first embodiment of a humidity regulating unit. The humidity regulating unit is installed inside an inhalation tube (not shown) for example near the patient of an inhalation circuit. For adult use, a tube with a diameter of about 22 mm is used in an artificial respirator to connect the patient's lungs (not shown) to an inhalation gas supply source (also not shown). Humidity regulating unit 1 includes a heating element 2 and a covering 3. The size of the humidity regulating unit 1 is, for example, about 18 to 20 mm in horizontal width, about 2 to 3 mm in thickness, and about 1 m in total length.

Figure 3:
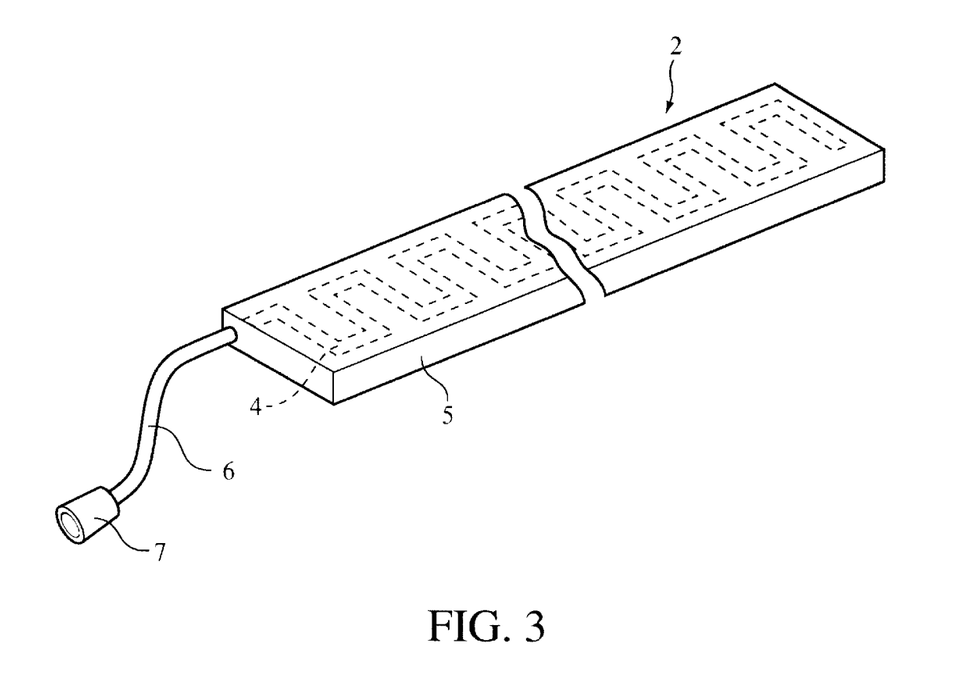
FIG. 3 is a perspective view of an electric heating element used in the humidity regulating unit of FIG. 1.

In this embodiment, as shown in FIG. 3, heating element 2 is a thin plate that has an extended shape with a rectilinear cross section, and has flat sides. Heating element 2 is an electric heating element, and to satisfy this electrical structure, heating element 2 includes a heating wire 4 (heater wire) and an insulator 5 that encloses the heating wire. Heating wire 4 is disposed inside insulator 5 and produces heat when supplied with an electric current. A coated connecting cord 6 connected to this heating wire 4 is drawn outward from one end of heating element 2, and a single current supply connector 7 is installed at the end of connecting cord 6. Insulator 5 is preferably a synthetic resin that has an insulating property.

Figure 1:
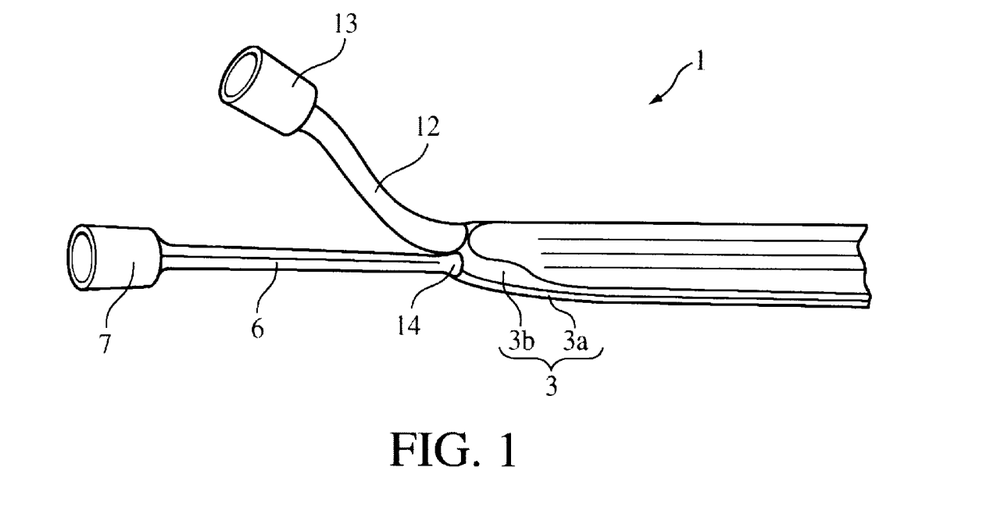
FIG. 1 is a perspective view of a humidity regulating unit according to a first embodiment of the present invention.

In this embodiment, covering 3 is formed by bonding, in a watertight laminated structure, two halves 3a and 3b that have porous retaining walls (having, for example, a porosity of about 57.8%) through which water does not pass but a gas, such as steam passes. In this embodiment, a resin, such as polytetrafluoroethylene, is used for covering 3. Covering 3 has a shape that corresponds to heating element 2, and houses heating element 2 therein tightly and completely.

Figure 2:
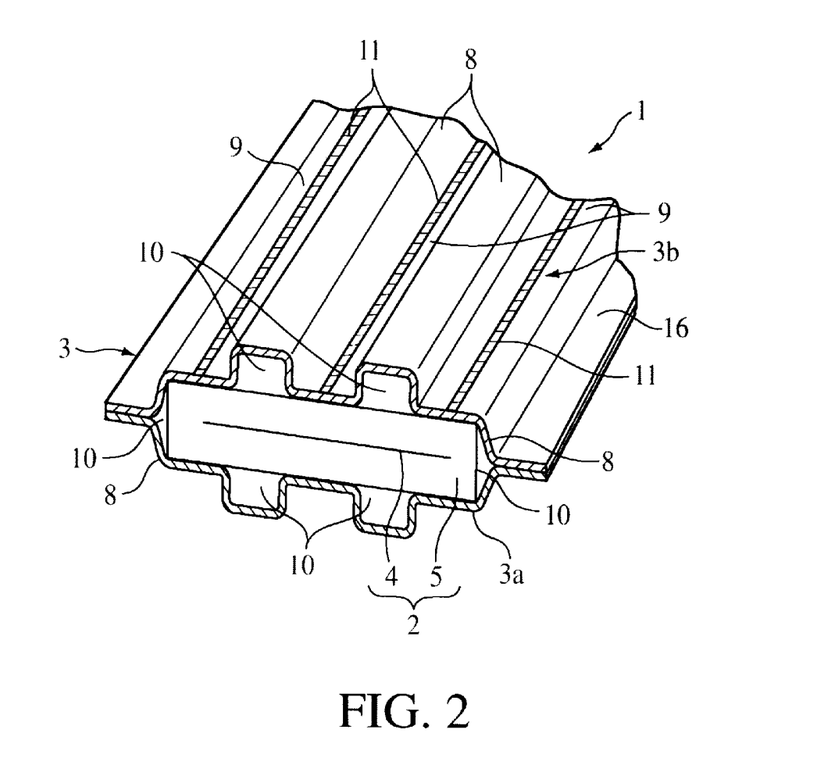
FIG. 2 is a perspective cross-sectional view that illustrates the internal structure of the humidity regulating unit of FIG. 1.

As shown in FIG. 2, several bulges 8 are formed on covering 3 to define the above-mentioned porous retaining wall. Bulges 8 extend along the length of covering 3. Each bulge 8 and the outer surface of heating element 2 defines a separate, independent water route 10 that extends along the length of heating element 2. In this embodiment, as shown in FIG. 2, water routes 10 are formed not only on the wide sides of heating element 2, but also on the thin sides. In addition, portions 9 of covering 3, other than bulges 8, are shaped such that they contact the outer surface of heating element 2, and these portions 9 are designed to support the mutual independence of adjacent water routes by contacting the outer surface of heating element 2. The opening on one side of each water route 10 (in FIG. 1, the left side) faces the inside of one side of covering 3 (in FIG. 1, the left side), and the opening on the other end of each water route 10 is sealed using covering 3.

Covering 3 and the outer surface of heating element 2 are bonded at portions 9. This bonding is performed along each water route 10 between adjacent water routes. In this embodiment, because a resin issued by covering 3 and the outer surface of heating element 2 (the surface of insulator 5) welding is used for this bonding. It is to be understood that other modes of bonding also may be used, such as adhesive.

As shown in FIG. 1, a water supply hose 12 is connected to covering 3. A connector 13 is provided at the end of water supply hose 12, and a water supply source connector (not shown) is connected to connector 13. Water from the water supply source is supplied to the inside of covering 3, and is further conducted to each water route 10. A cord insertion hole 14 is formed on one end of covering 3. Connecting cord 6 is drawn through cord insertion hole 14, and this maintains adequate watertightness between connecting cord 6 and covering 3. A current supply connector (not shown) is connected form the current source to current supply connector 7 on the end of connecting cord 6. As a result, current can be supplied to heating wiring 4 so that each water route 10 is heated by heat radiated from heating wire 4, and steam can be expelled from each water route 10 through covering 3 to the inhalation gas inside the inhalation tube. The present invention contemplates that the amount of steam expelled is regulated automatically based on the difference between the steam pressure inside water routes 10 and the steam pressure inside the inhalation tube.

However, as a result of the operation of electric heating element 2, the temperature of the inhalation gas is set and does not rise above a particular temperature which is preferably a temperature that is uncomfortable for the patient.

Therefore, in humidity regulating unit 1, when water is supplied to each water route 10 and heated by heating element 2, steam is expelled from each water route to the gas outside the water route by way of the porous retaining wall, and the desired humidifying performance can be achieved under optimum conditions.

In addition, because the outer surface of heating element 2 is used as part of the walls of water routes 10 and heating element 2 does not have to be housed inside of water routes 10, the size of heating element 2 does not restrict making the cross section of each water route 10 as small as possible. As a result, even if covering 3 breaks or is damaged, the amount of water leaking from water routes 10 that this covering 3 covers is extremely small, thereby minimizing any reduction in humidifying performance or problems associated with water leakage.

Furthermore, because each water route 10 is defined by a bulge 8 and the outer surface of heating element 2 that covers the open base of bulge 8, the surface area of the steam emitting surface of covering 3 is increased, and humidifying performance is maximized.

In addition, because a resin is used for both covering 3 and the outer surface of electric heating element 2, covering 3 can be welded to the outer surface of heating element 2, insulator 5 of electric heating element 2 can be used to bond covering 3 and the outer surface of electric heating element 2 thereby simplifying the manufacturing process.

The method of manufacturing humidity regulating unit 1 is described below with reference to FIGS. 4 and 5. First, two halves 3a and 3b have porous retaining walls through which water does not pass but steam passes and electric heating element 2 are prepared. Each half 3a and 3b includes bulges 8, a depression 15 for housing heating element 2, and a connecting flange 16.

Figures 4, 5:
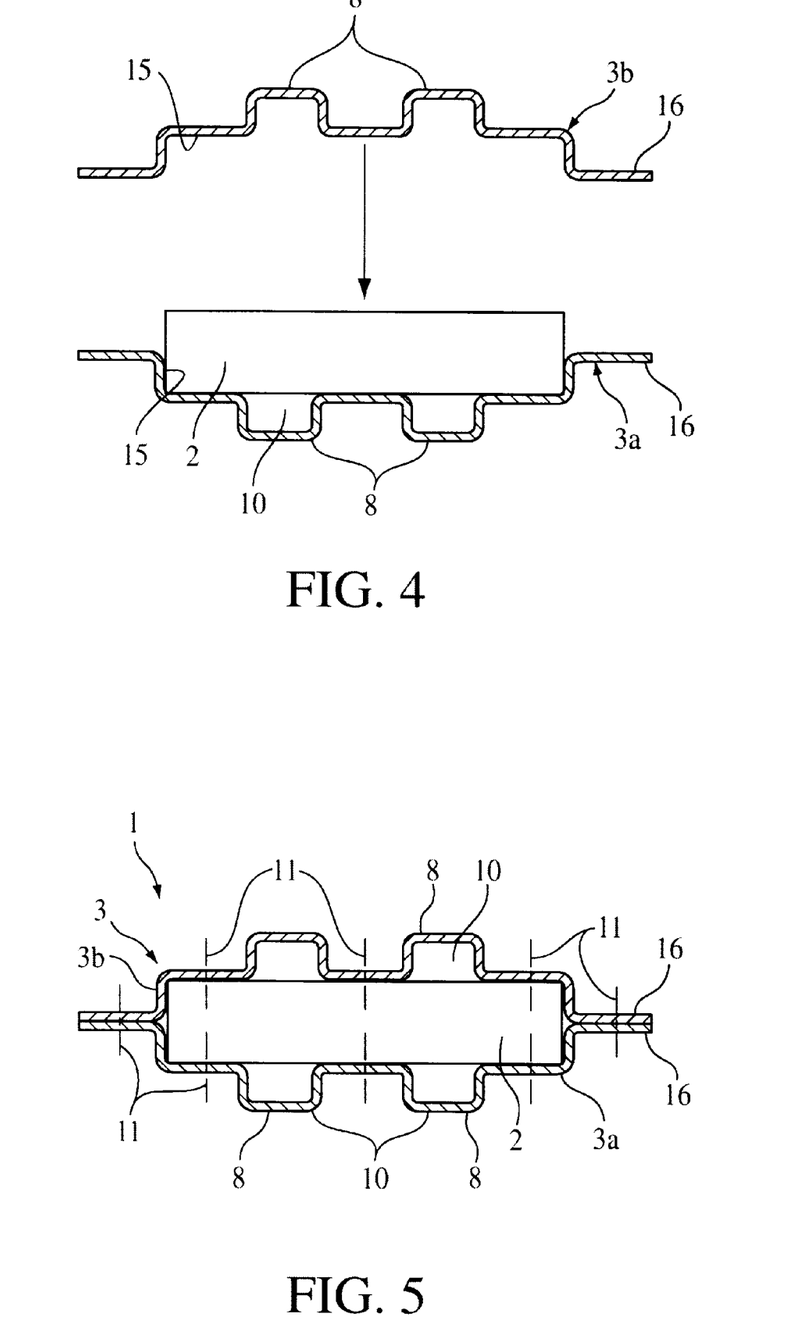
FIG. 4 is a cross-sectional view illustrating a method for manufacturing the humidity regulating unit of FIG. 1.
FIG. 5 is a cross-sectional view illustrating a manufacturing step that follows the step shown in FIG. 4.

Next, heating element 2 is disposed in depression 15 in one half 3a of covering 3, as shown in FIG. 4. At this time, connecting cord 6 is drawn outside by way of cord insertion hole 14 which itself is divided into two halves.

Next, the other half 3b of covering 3 is laminated to the first half 3a, as shown in FIGS. 4 and 5. This houses heating element 2 in the internal space between the two halves 3a and 3b, and also forms several water routes between the outer surface of heating element 2 and two halves 3a and 3b.

Next, connecting flanges 16 are welded (bonded) together as shown in FIG. 5, the outer surface or heating element 2 and each of halves 3a and 3b are welded at bonding sites between adjacent water routes 10, to complete humidity regulating unit 1.

Thus, according to this method of manufacture, humidity regulating unit 1 can be manufactured easily, simply by placing heating element 2 between two halves 3a and 3b, then welding halves 3a and 3b together and welding halves 3a and 3b to heating element 2.

FIGS. 6 to 10 illustrate a second embodiment of a humidity regulating unit 1'. In this second embodiment, structural elements that are the same as the first mode of embodiment described above are labeled by the same part numbers and their explanation is not repeated.

Figure 6:
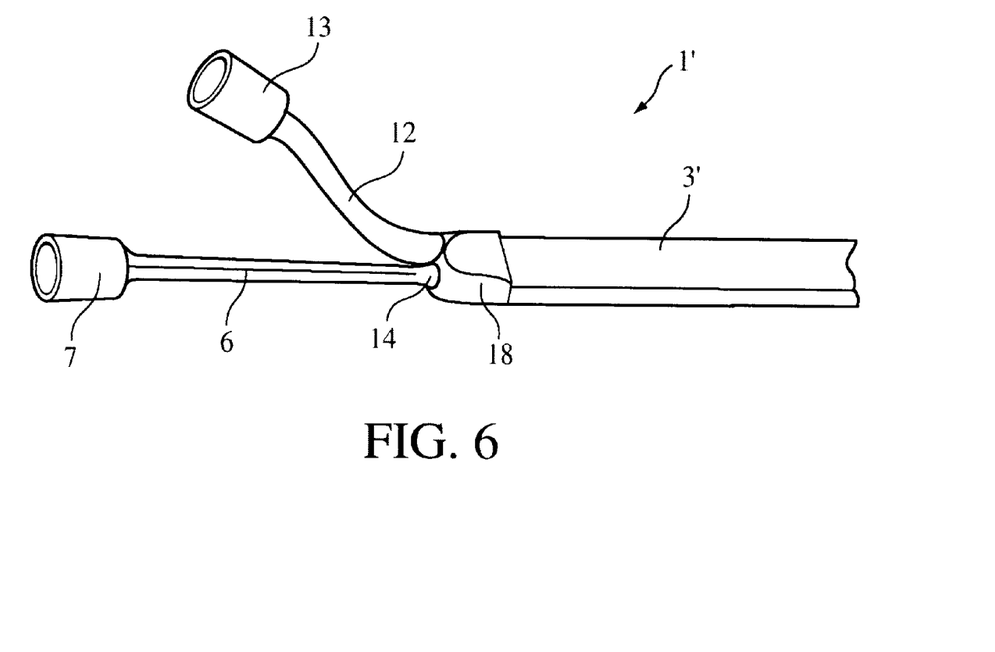
FIG. 6 is a perspective view of a humidity regulating unit according to a second embodiment of the present invention.
Figure 7:
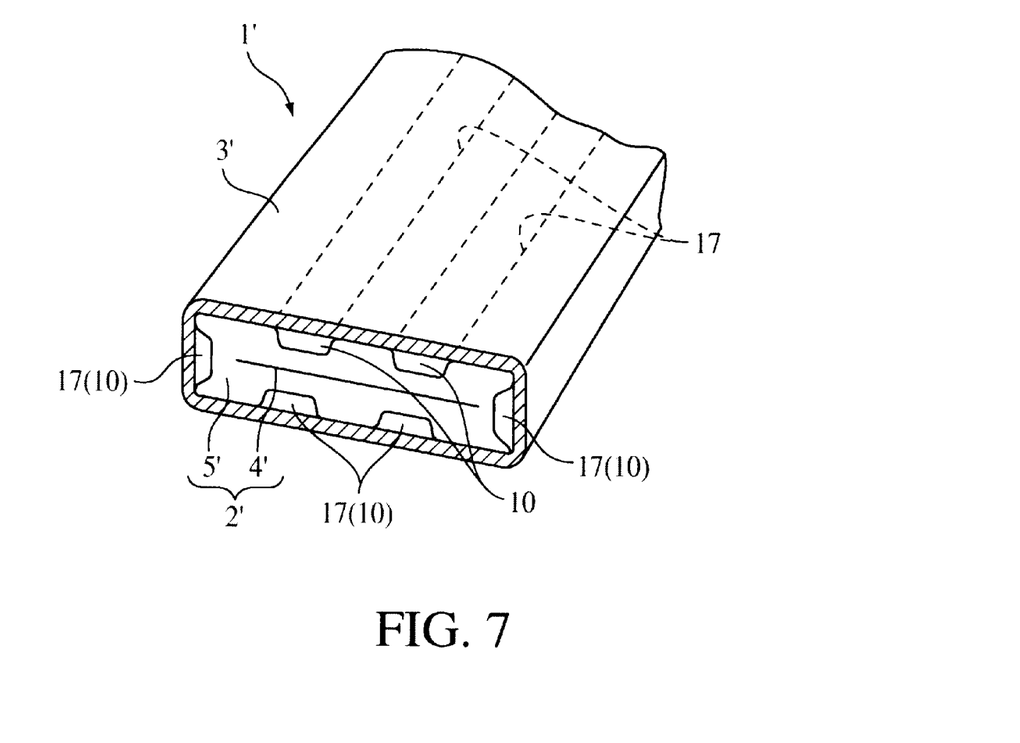
FIG. 7 is a perspective cross-sectional view that illustrates the internal structure of the humidity regulating unit of FIG. 6.

In humidity regulating unit 1', channels 17 are formed in succession by defining spaces in the outer surface of electric heating element 2' along the circumference of the heating element. Covering 3' is a tube that surrounds electric heating element 2'. Each channel 17 and the portion of covering 3' that covers the opening of each channel defines each several water routes 10. A cap 18 is placed on the opening of covering 3', and the opening of cap 18 engages the opening of covering 3'. As a result, the open end of cover 3' is closed. A water supply hose 12 is connected to cap 18, a cord insertion hole 14 is formed in cap 18, and a connecting cord 6 for electric heating element 2' is inserted in a watertight manner through cord insertion hole 14.

In humidity regulating unit 1', not only are the problems in prior art devices associated with maintaining humidifying performance when a water channel is broken, solved in the same way as in the first embodiment, but the proportion of heating element 2' that constitutes the walls of each water route 10 is increased to increase the stability of the shape of each water route 10 and the stability of humidifying performance.

Figure 8:
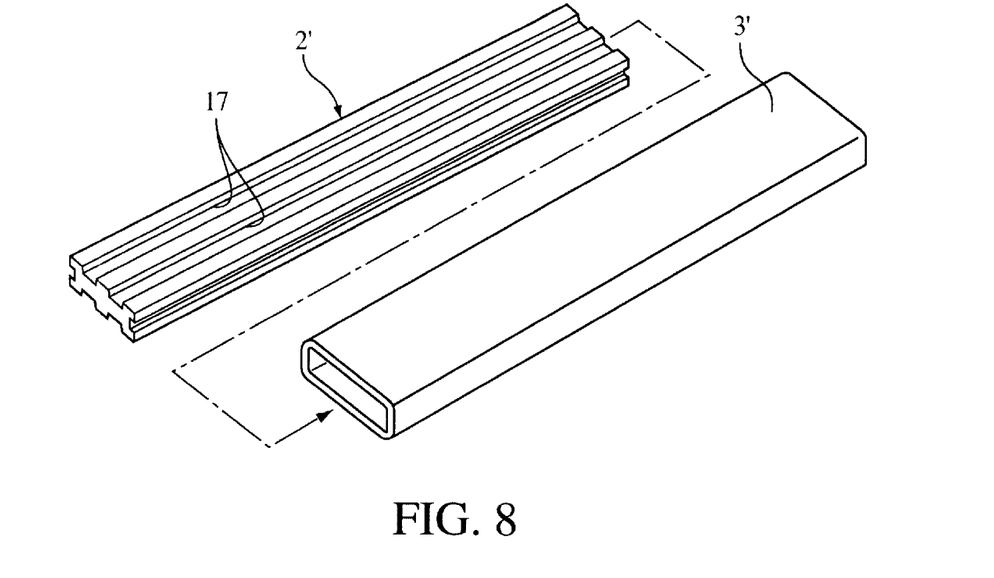
FIG. 8 illustrates the method for manufacturing the humidity regulating of FIG. 6.
Figure 9:
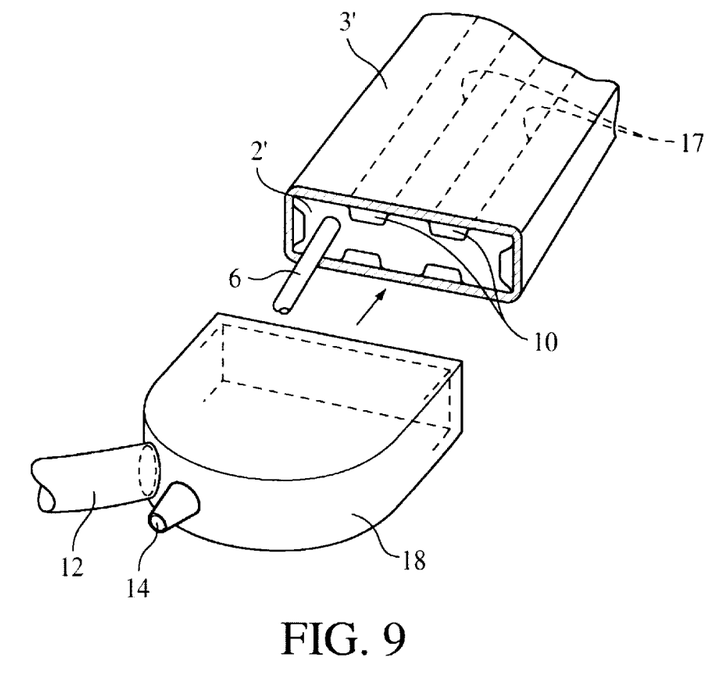
FIG. 9 is a perspective view that illustrates the manufacturing step that follows the step shown in FIG. 8.
Figure 10:
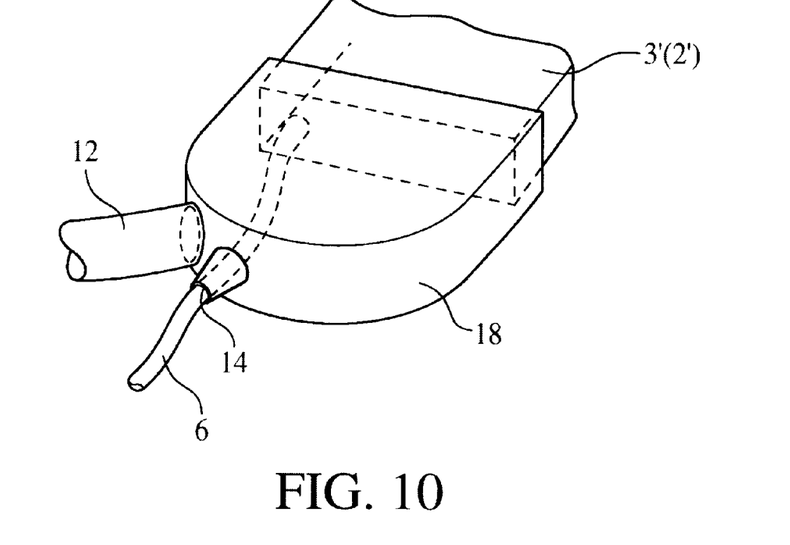
FIG. 10 is a perspective view that illustrates the manufacturing step that follows the step shown in FIG. 9.

Humidity regulating unit 1' is manufactured by first preparing tubular covering 3', cap 18 that can close the opening of covering 3' and has water supply hose 12 and cord insertion hole 14, and electric heating element 2' that has channels 17 formed in succession on the outer surface along it circumference as described above. Next, electric heating element 2' is placed inside covering 3', as shown in FIG. 8, and water routes 10 are formed by covering 3' overlying each channel 17. Next, as shown in FIGS. 9 and 10, connecting cord 6 is inserted into cord insertion hole 14 of cap 18, then cap 18 is engaged over the opening of covering 3' and the opening of cap 18 and the opening of covering 3' are bonded. As a result, the opening of covering 3 is closed to complete, humidity regulating unit 1'. According to this method of manufacture, the humidity regulating unit is manufactured in a very efficient manner simply placing heating element 2' inside covering 3'.

Figure 11:
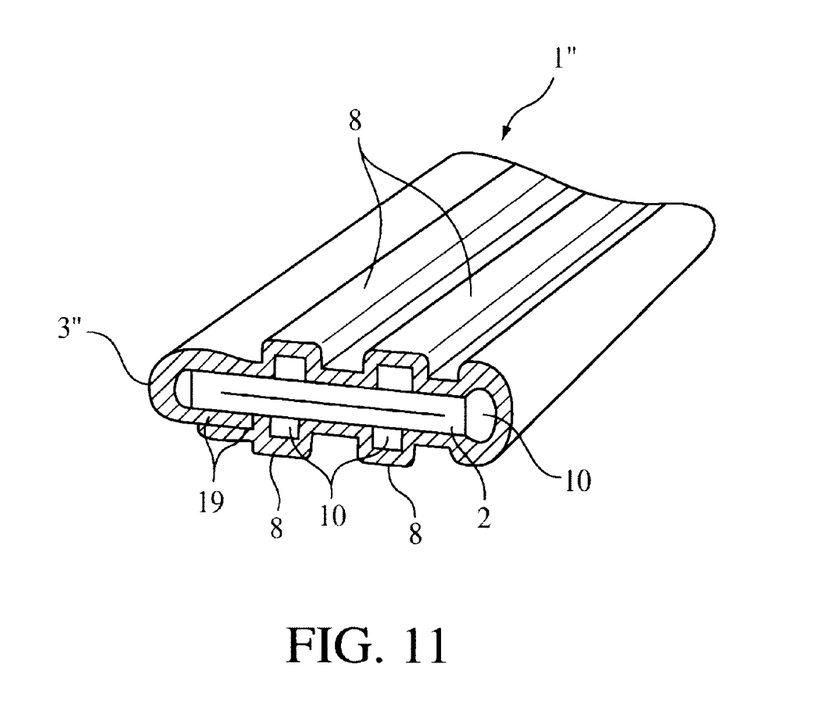
FIG. 11 is a perspective cross-sectional view that illustrates the internal structure of a humidity regulating unit according to a third embodiment of the present invention.

FIG. 11 shows a third embodiment of a humidity regulating unit 1". This third embodiment is a variant of the first embodiment described above. Therefore, in this third embodiment, structural elements that are the same as the first mode of embodiment described above are labeled by the same part numbers and their explanation is not repeated.

In this third embodiment, instead of using two halves 3a and 3b for covering 3", as in the first mode of embodiment described above, a single sheet is used for covering 3". The sheet is wrapped around heating element 2, and in addition to bonding portions 9 to the outer surface of heating element 2, ends 19 where the wrapping meets also are bonded. By using a single sheet as covering 3", part control and assembly operations can be simplified.

In the second and third embodiments described above, to maintain the independence of each water route 10, a structure is preferred in which heating element 2, 2' is placed tightly (i.e. in a watertight manner) within covering 3', 3". Furthermore, covering 3', 3" and heating element 2, 2' also can be bonded between adjacent water routes 10 as shown in the first embodiment (bonding sites 11).

What is claimed is:
1. A humidity regulating unit comprising:
a heating element; and
a covering disposed over at least a portion of the heating element such that a plurality of independent and discrete fluid carrying channels are defined along a surface of the heating element, each fluid carrying channel being defined by the surface of the heating element and a portion of the covering overlying the heating element, and wherein the covering is defined by a material that prevents a liquid from passing therethrough while allowing a gas to pass therethrough, so that a liquid in a first fluid carrying channel cannot pass to a second fluid carrying channel in the plurality of fluid carrying channels.

2. The humidity regulating unit of claim 1, wherein the covering is disposed over the heating element such that a plurality of bulges are defined by the covering overlying the surface of the heating element and protruding outward therefrom, with each bulge in the covering and an underlying surface of the heating element defining a fluid carrying channel.

3. The humidity regulating unit of claim 2, wherein the heating element includes a substantially flat surface over which the covering is disposed.

4. The humidity regulating unit of claim 1, wherein the surface of the heating element over which the covering is disposed includes a plurality of channels defined therein, with each channel in the surface of the heating element and an overlying portion of the covering defining a fluid carrying channel.

5. The humidity regulating unit of claim 4, wherein a portion of the covering overlying the channel in the surface of the heating element is substantially flat.

6. The humidity regulating unit of claim 1, wherein the covering and the surface of the heating element are bonded together between adjacent fluid carrying channels to define the independent and discrete fluid carrying channels.

7. The humidity regulating unit of claim 6, wherein the surface of the heating element is defined by a coated resin, and wherein the bond between the covering and the surface of the heating element is defined by a weld between the coated resin and the covering.

8. The humidity regulating unit of claim 1, wherein the heating element is an electric heating element.

9. A pressure support system comprising:
a pressure generator adapted to provide a flow of breathing gas;
a conduit having a first end coupled to the pressure generator and a second end, wherein the conduit is adapted to deliver the flow of breathing gas to an airway of a patient; and
a humidity regulating unit adapted to be disposed in the conduit so as to humidify the flow of breathing gas being delivered to the patient, the humidity regulating unit comprising:
a heating element; and
a covering disposed over at least a portion of the heating element such that a plurality of independent and discrete fluid carrying channels are defined along a surface of the heating element, each fluid carrying channel being defined by the surface of the heating element and a portion of the covering overlying the heating element, and wherein the covering is defined by a material that prevents a liquid from passing therethrough while allowing a gas to pass therethrough, so that a liquid in a first fluid carrying channel cannot pass to a second fluid carrying channel in the plurality of fluid carrying channels.

10. The pressure support system of claim 9, wherein the covering is disposed over the heating element such that a plurality of bulges are defined by the covering overlying the surface of the heating element and protruding outward therefrom, with each bulge in the covering and an underlying surface of the heating element defining a fluid carrying channel.

11. The pressure support system of claim 9, wherein the surface of the heating element over which the covering is disposed includes a plurality of channels defined therein, with each channel in the surface of the heating element and an overlying portion of the covering defining a fluid carrying channel.

12. A method of manufacturing a humidity regulating unit, comprising:
providing a covering defined by a material that prevents a liquid from passing therethrough while allowing a gas to pass therethrough;
disposing the covering over a heating element such that a plurality of independent and discrete fluid carrying channels are defined along a surface of the heating element by the surface of the heating element and a portion of the covering overlying the heating element; and
bonding the covering to the heating element between adjacent fluid carrying channels to form the discrete fluid carrying channels overlying the heating element.

13. The method of claim 12, wherein disposing the covering over a heating element includes forming a plurality of bulges in the covering overlying the surface of the heating element and protruding outward therefrom, with each bulge in the covering and an underlying surface of the heating element defining a fluid carrying channel.

14. The method of claim 13 further comprising forming the heating element such that the heating element includes a substantially flat surface.

15. The method of claim 12, further comprising defining a plurality of channels in the surface of the heating element, such that channel in the surface of the heating element and an overlying portion of the covering defines a fluid carrying channel in the assembled humidity regulating unit.

16. The method of claim 15, wherein the portion of the covering overlying the channel in the surface of the heating element is substantially flat.

17. A method of manufacturing a humidity regulating unit, comprising:
providing a tubular covering defined by a material that prevents a liquid from passing therethrough while allowing a gas to pass therethrough;
inserting a heating element into the tubular covering;
bonding the covering to the heating element such that a plurality of independent and discrete fluid carrying channels are defined along a surface of the heating element by the surface of the heating element and a portion of the covering overlying the heating element, with the covering and the heating element being bonded together between adjacent fluid carrying channels to form the discrete fluid carrying channels overlying the heating element; and
sealing the ends of the tubular covering.

18. The method of claim 17, wherein the covering and heating element are sized and configured such that a plurality of bulges are formed in the covering overlying the surface of the heating element and protruding outward therefrom, with each bulge in the covering and an underlying surface of the heating element defining a fluid carrying channel.

19. The method of claim 18, further comprising forming the heating element such that the heating element includes a substantially flat surface.

20. The method of claim 17, further comprising defining a plurality of channels in the surface of the heating element, such that the channel in the surface of the heating element and an overlying portion of the covering defines a fluid carrying channel in the assembled humidity regulating unit.

21. The method of claim 20, wherein the portion of the covering overlying the channel in the surface of the heating element in the assembled humidity regulating unit is substantially flat.

* * * * *